United States Patent
Tsai (12)

(10) Patent No.: US 6,352,729 B1
(45) Date of Patent: Mar. 5, 2002

(54) PLANT EXTRACT THAT INHIBITS THE RELEASE OF TUMOR NECROSIS FACTOR ALPHA (TNF-ALPHA)

(75) Inventor: David M Tsai, Westlake Village, CA (US)

(73) Assignee: Ambryx Biotechnology, Inc., Irvine, CA (US)

( * ) Notice: Subject to any disclaimer, the term of this patent is extended or adjusted under 35 U.S.C. 154(b) by 0 days.

(21) Appl. No.: 09/698,959

(22) Filed: Oct. 30, 2000

(51) Int. Cl.$^7$ ................................................ A61K 35/78
(52) U.S. Cl. ....................................... 424/777; 424/725
(58) Field of Search .................................. 424/725, 777

(56) References Cited

FOREIGN PATENT DOCUMENTS

JP        09-315938  A   *   9/1997

OTHER PUBLICATIONS

Novogrodsky, A., et al., Prevention of Lipopolysaccharide–Induced Lethal Toxicity by Tyrosine Kinase Inhibitors, Science, May 27, 1994, p. 1319, vol. 264,.

Tracy, K.J., et al., Anti–cachectin/TNF monoclonal antibodies prevent septic schock during lethal bacteraemia, Nature, Dec. 17, 1987, p. 662, vol. 330.

Beutler, B., et al., Passive Immunization Against Cachectin/Tumor Necrosis Factor Protects Mice from Lethal Effect of Endotoxin, Science, Aug. 30, 1985, p. 869, vol. 229.

Mathison, John C., et al., Participation of Tumor Necrosis Factor in the Mediatin of Gram Negative Bacterial Lipopolysaccharide–induced injury in Rabbits, J. Clin. Invest., Jun. 1988, p. 1925, vol. 81.

Grau, G.E., et al., Tumor Necrosis Factor (Cachectin) as an Essential Mediator in Murine Cerebral Malaria, Science, Sep. 4, 1987, p. 1210, vol. 237.

Cayer, J.M., et al., Cachectin/Tumor Necrosis Factor Stimulates Collagenase and Prostaglandin $E_2$ Production by Human Synovial Cells and Dermal Fibroblasts, J. Exp. Med., Dec. 1985, p. 2163, vol. 162, The Rockefeller Univ. P.

Haddad, E.K., et al., Early Embryo Loss is Associated with Local Production of Nitric Oxide by Decidual Mononuclear Cells, J. Exp. Med., Oct. 1995, p. 1143. vol. 182, The Rockefeller Univ. Press.

Wei, X.Q., et al., Altered Immune Responses in Mice Lacking Inducible Nitric Oxide Synthase, Nature, Jun. 1, 1995, p. 408, vol. 375.

Spriggs, David, et al., Genomic Structure, Induction, and Production of TNF–60 , Chapter 1 in "Tumor Necrosis Factor", Marcel Dekker Inc.

Trentham, David E., et al., Autoimmunity to Type II Collagen: an Experimental Model of Arthritis, J. Exp. Med., 1977, p. 857, vol. 146., The Rockefeller Univ. Press.

Bertolini, Donald R., et al., Stimulation of Bone Rescrption and Inhibition of Bone Formation in Vitro by Human Tumour Necrosis Factors, Nature, Feb., 1986, p. 516, vol. 319.

Keffer, J., et. al., Transgenic Mice Expressing Human Tumour Necrosis Factor: a predictive genetic model of arthritis, EMBO J., 1991, pp. 4025–4031, vol. 10, Oxford University Press.

Taylor, G., et. al., A Pathogenic Role for TNF alpha in the Syndrome of Cachexia, Arthritis, and Autoimmunity Resulting from Tristetraprolin (TTP) Deficiency, Immunity, May 1996, pp. 445–454, vol. 4, Cell Press.

Elliott, M., et. al., Repeated Therapy with Monoclonal Antibody to Tumour Necrosis Factor alpha (cA2) in Patients with Rheumatoid Arthritis, The Lancet, pp. 1125–1127, Oct. 22, 1994, vol. 344.

Chomczynski, P., et. al., Single–Step Method of RNA Isolation by Acid Guanidinium Thiocyanate–Phenol–Chloroform Extraction, Analytical Biochemistry, pp. 156–159, 1987, vol. 162, Academic Press, Inc.

Aviv, H., et. al., Purification of Biologically Active Globin Messenger RNA by Chromatography on Oligothymidylic acid–Cellulose, Proc. Nat. Acad. Sci., pp. 1408–1412, Jun. 1972. vol. 69.

Kriegler, M., et. al., A Novel Form of TNF/Cachectin Is a Cell Surface Cytotoxic Thransmembrane Protein: Ramifications for the Complex Physiology of TNF, Cell, pp. 45–53, Apr. 8, 1988, vol. 53, Cell Press.

\* cited by examiner

*Primary Examiner*—Christopher R. Tate
*Assistant Examiner*—Kailash C. Srivastava
(74) *Attorney, Agent, or Firm*—Trojan Law Offices

(57) ABSTRACT

An extract from the Melothria Indica Lou plant, which has the effect of inhibiting the release of cytokines, including Tumor Necrosis Factor-alpha, by immune response cells, such as macrophages, for the therapeutic treatment of sepsis.

4 Claims, 7 Drawing Sheets

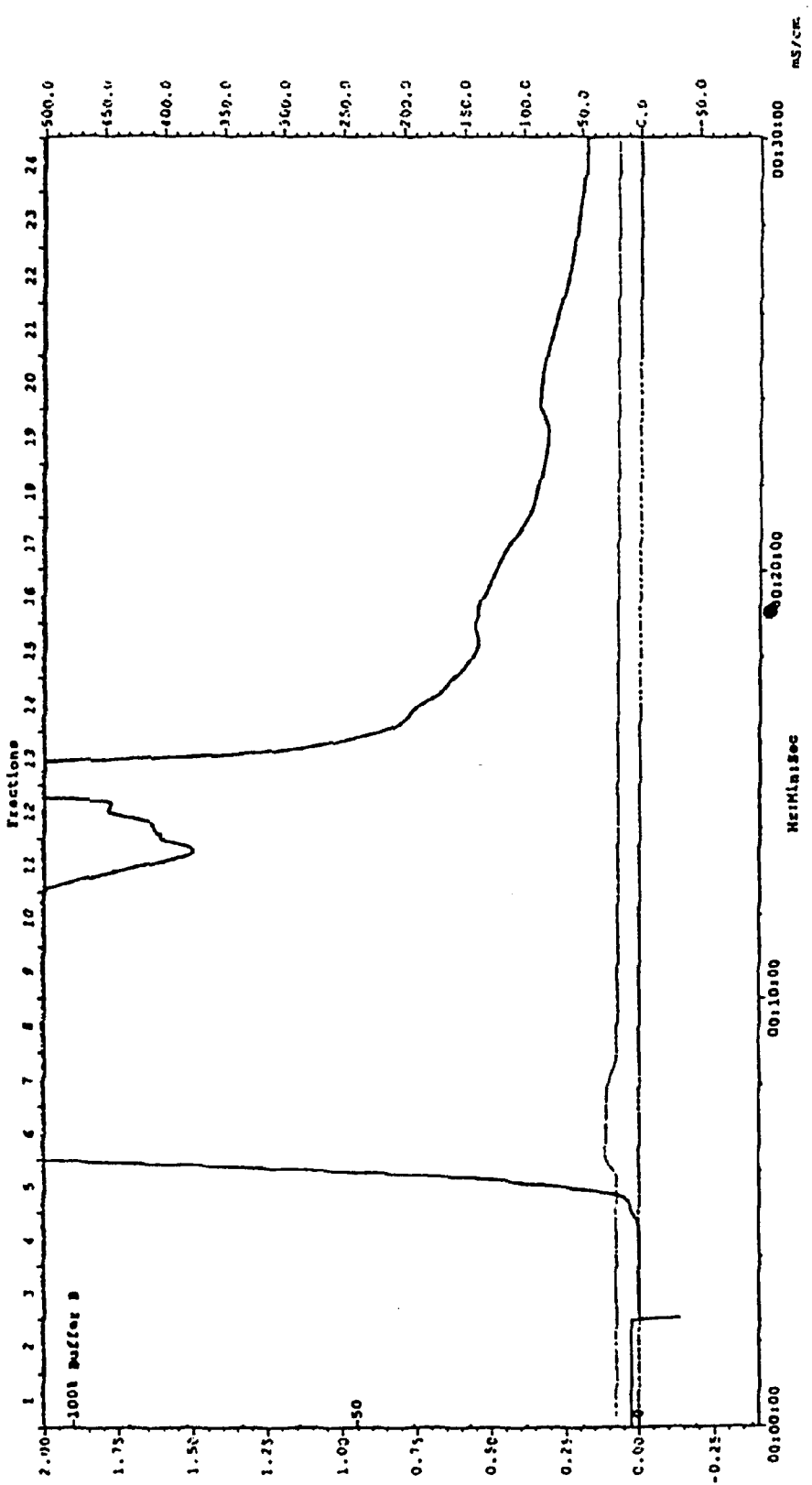
FIG. 1: SCD Reverse-Phase Chromatography (PBS Elution) of the Extract of Melothria Indica Lou.

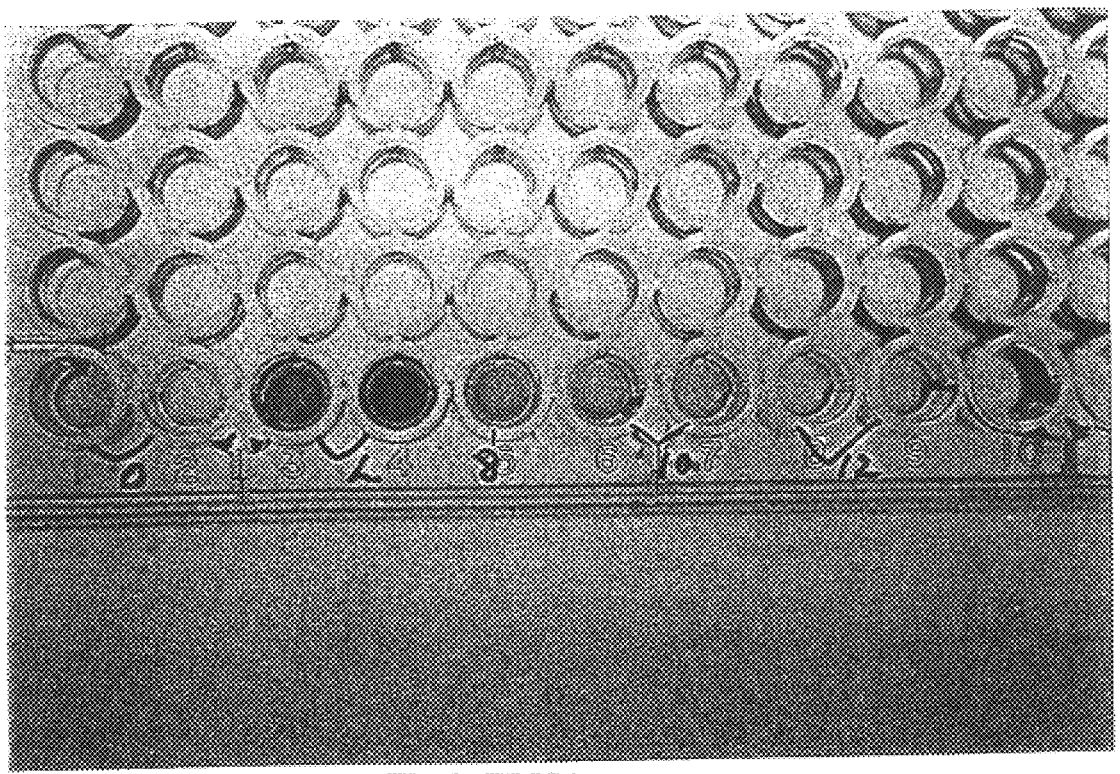
Fig.2 ELISA assay

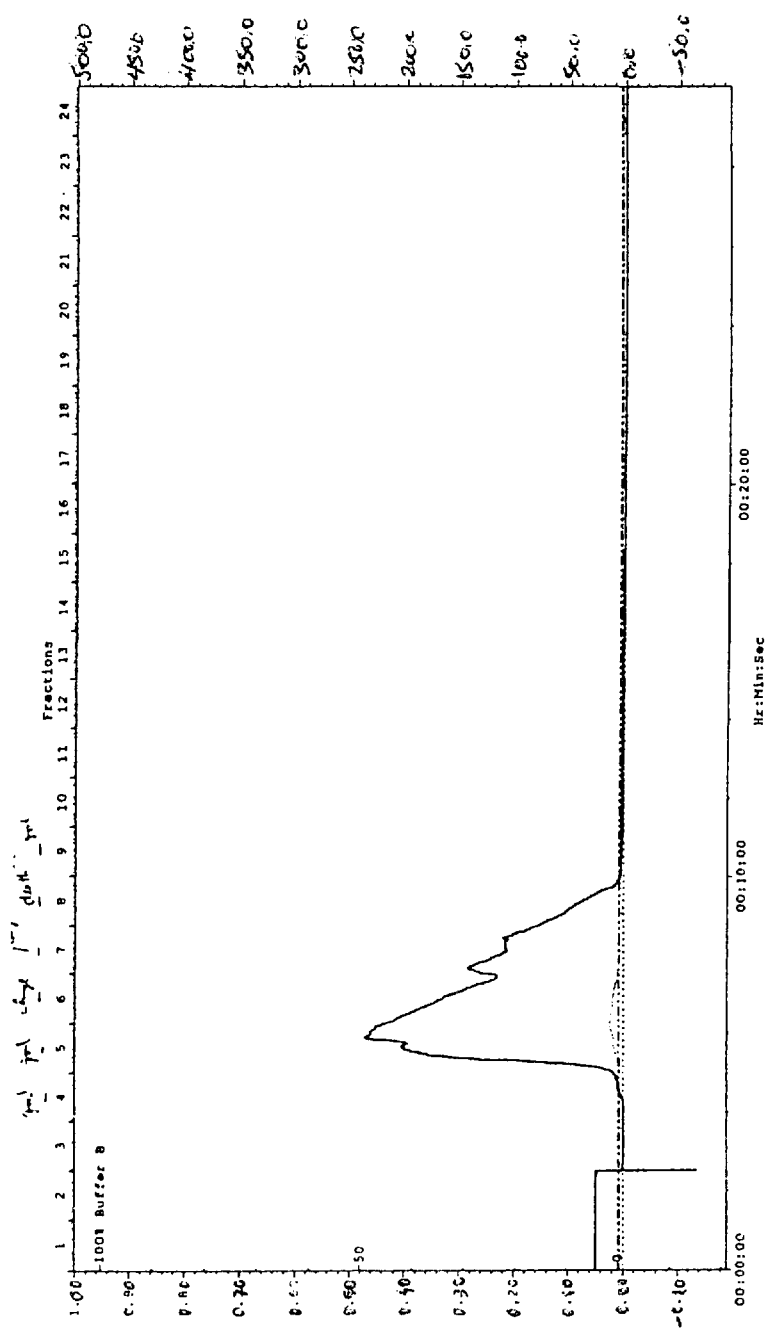
Fig.3 SCD reverse-phase chromatography (organic solvent elution)

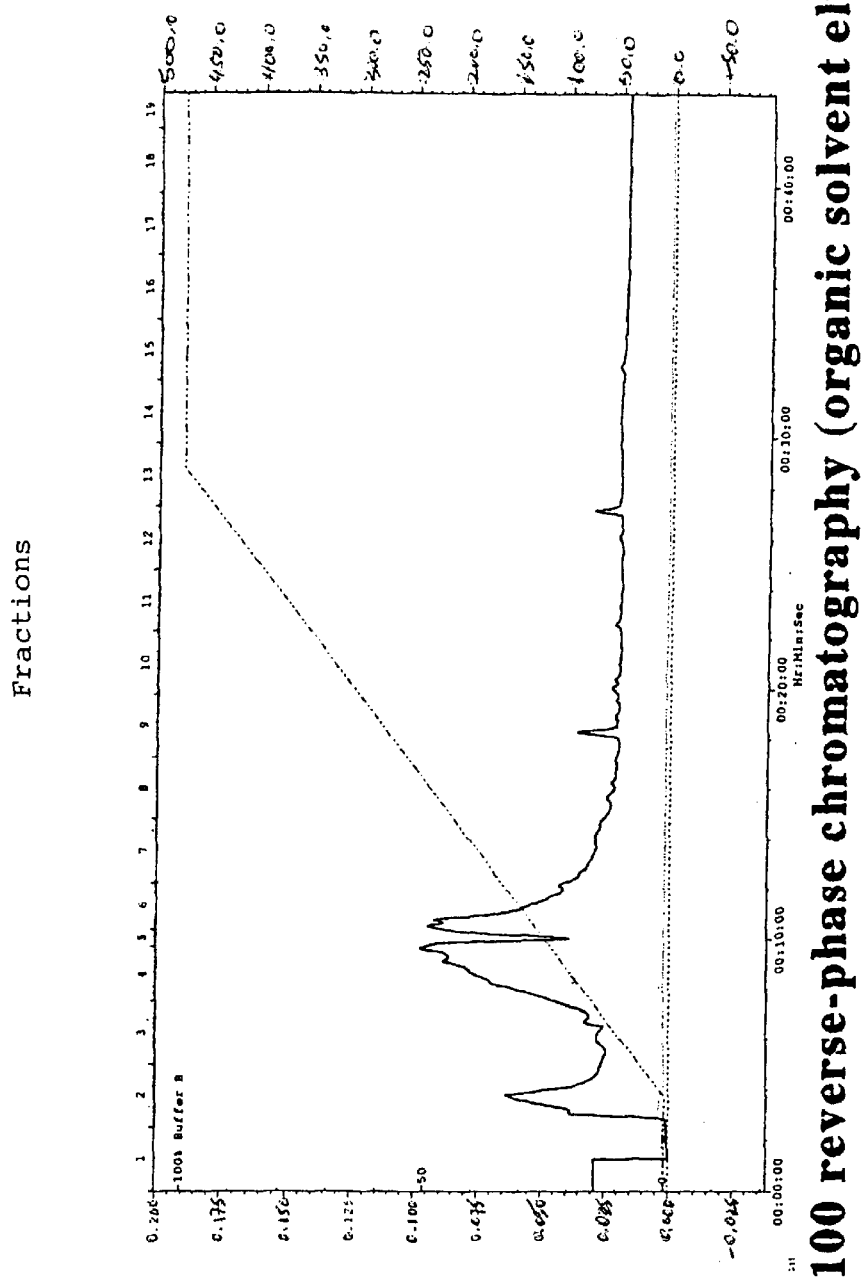
Fig. 4. RPP-100 reverse-phase chromatography (organic solvent elution).

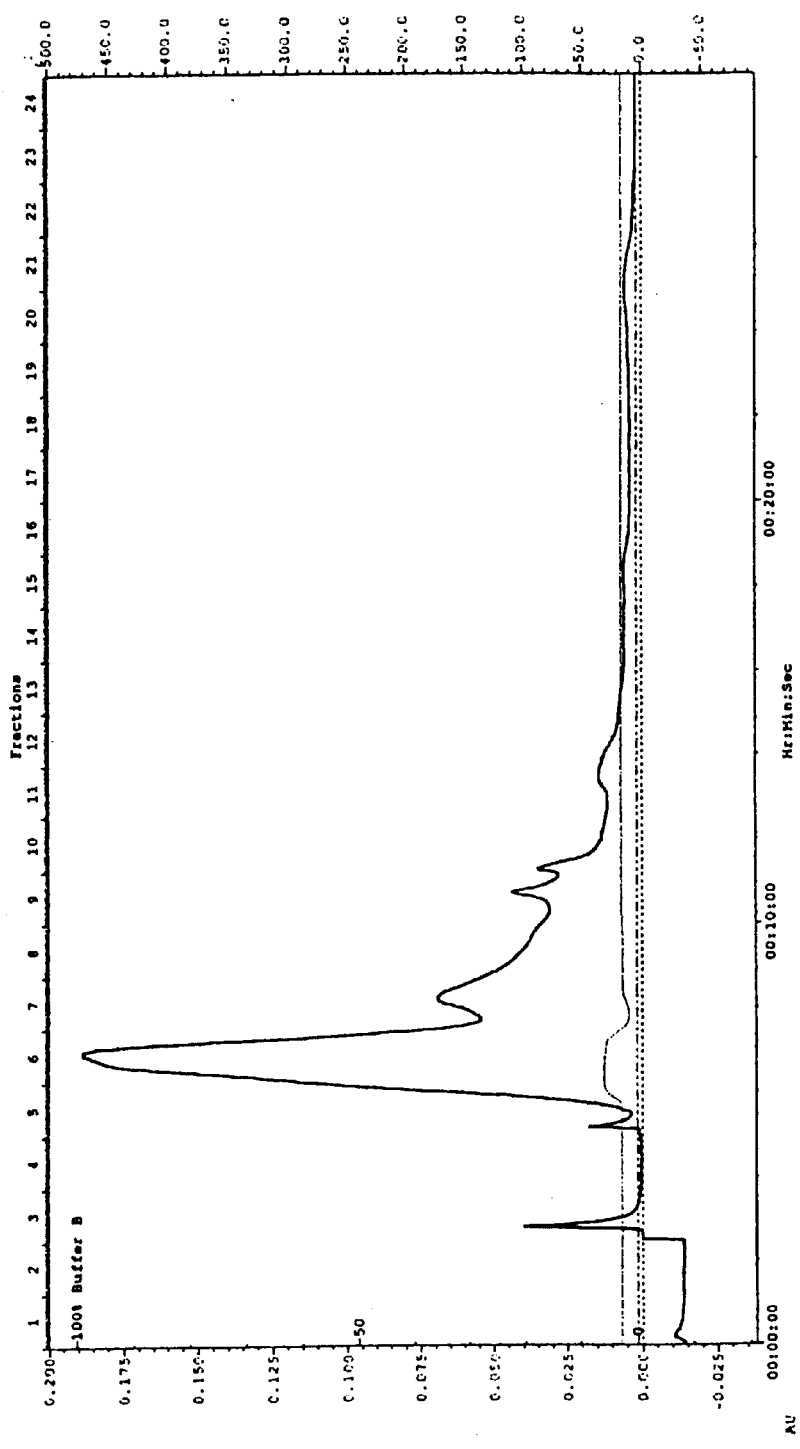
Fig. 5. AX-100 anion exchange chromatography (PBS elution)

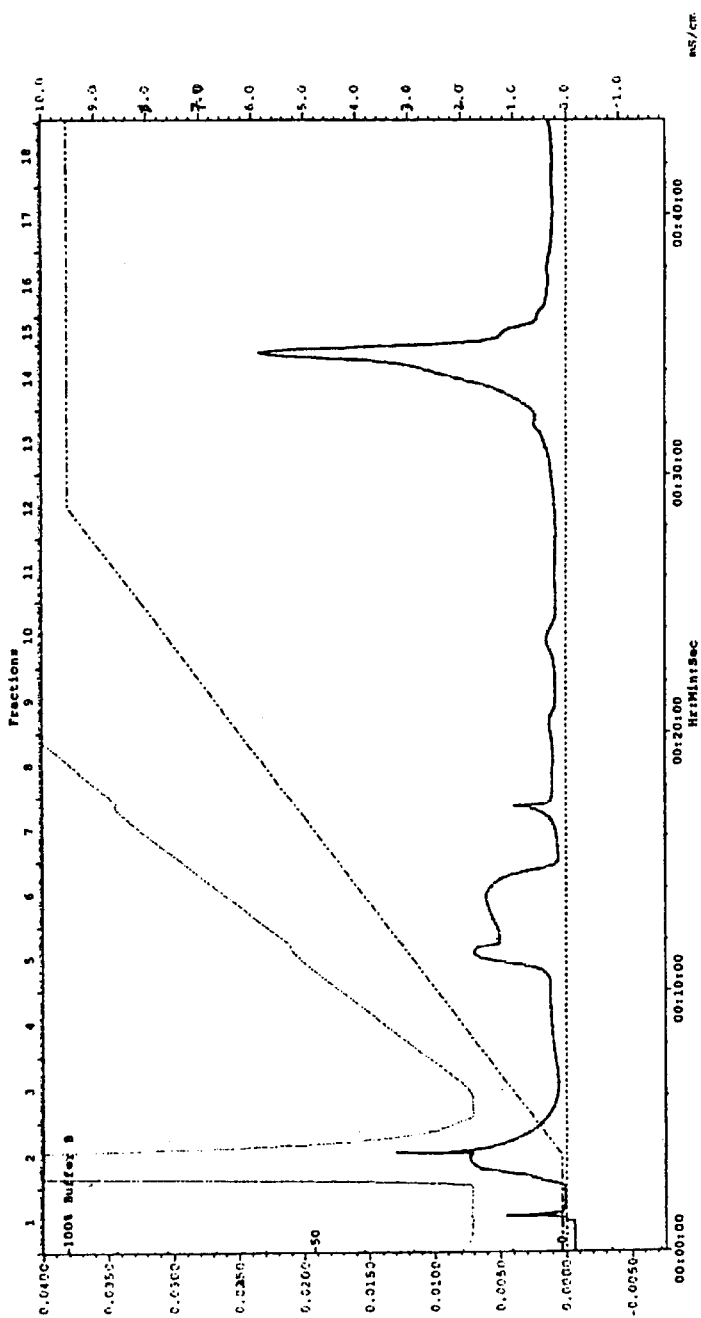
Fig.6. AX-100 anion exchange chromatography (PBS gradient elution)

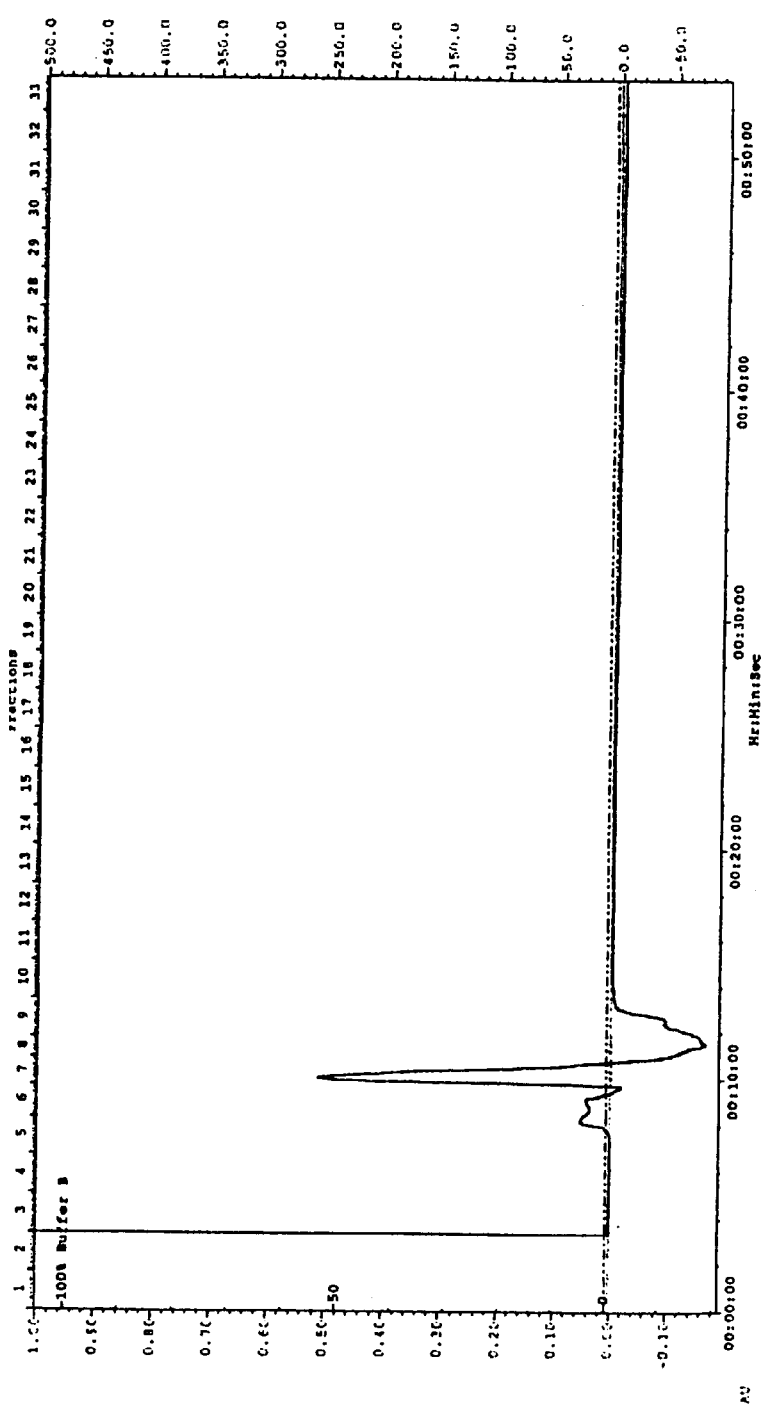
Fig.7. Silica gel adsorption chromatography

PLANT EXTRACT THAT INHIBITS THE RELEASE OF TUMOR NECROSIS FACTOR ALPHA (TNF-ALPHA)

BACKGROUND OF THE INVENTION

This invention relates to a naturally occurring extract Kas from the Melothria Indica Lou plant that inhibits the release of cytokines such as Tumor Necrosis Factor-alpha (TNF-alpha) by immune response cells, such as macrophages, for the therapeutic treatment of disease including sepsis.

Many of the toxic effects of endotoxins can be mimicked in vivo by TNF-alpha or IL-1 beta themselves (Norogrodsky, et. al., 1994, Science 264:1319). Tumor necrosis factor-alpha (TNF-alpha), a 17 Kda protein produced by macrophages and other cells, was discovered by separate groups of investigators pursuing mediators of disparate diseases. The pleiotropic nature of TNF-alpha prevents generalization about whether it is beneficial or injurious. It is clear that, in some instances, the local effects of TNF-alpha improve host defense mechanisms by mobilizing substrate, increasing immune cell function, and stimulating inflammation. But, in other cases, the toxicity of TNF-alpha may cause disease by mediating septic shock, tissue injury, or catabolic illness. TNF-alpha has been implicated in many diseases including: AIDS, Anemia, Autoimmune Disease, Cachexia, Cancer, Cerebral Malaria, Diabetes Mellitus, Disseminated Intravascular Coagulopathy, Eurthyroid Sick Syndrome, Hemorrhagic Shock, Hepatitis, Insulin Resistance, Leprosy, Leukemia, Lymphoma, Meningitis, Multiple Sclerosis, Myocardial Ischemia, Obesity, Rejection Of Transplanted Organs, Rheumatoid Arthritis, Septic Shock, Stroke and Tuberculosis (Tracey, K. J., *Tumor Necrosis Factor-alpha* in The Cytokine Handbook (Academic Press Limited 1994)).

Septic Shock Syndrome, a frequently lethal complication of infectious disease, kills 85,000–150,000 people in the USA annually (Tracey, K. J., *Tumor Necrosis Factor-alpha* in The Cytokine Handbook (Academic Press Limited 1994)). This disease is caused by a massive systemic infection by Gram-negative bacteria. Due to excessive stimulation of the host immune system by the endotoxin lipopolysaccharide (LPS), which is present on the outer membrane of the bacteria, the host immune cells, mainly macrophages, produce several cytokines such as Tumor Necrosis Factor-alpha (TNF-alpha), Interleukin 1-Beta (IL-I Beta), Interleukin 6 (IL-6) and Nitric Oxide (NO), which are the main modulators of the response to LPS (Norogrodsky, et. al., 1994, Science 264:1319). It has been reported that anti-TNF monoclonal antibodies prevent the development of septic shock in animal studies (Tracey, et. al., 1987, Nature 330:66; Beutler, 1985, Science 229:869; Mathison, et. al., 1988, J. Clin. Invest. 81:1925; Grau, et. al., 1987, Science 237:1210). These findings provide a rationale for the removal of TNF for the purpose of the treatment of sepsis shock. We have discovered a component designated as Kas from the extract of plant Melothria Indica Lou that functionally removed TNF-alpha by blocking the release of TNF-alpha by macrophage. In a sepsis animal model, we found that Kas prevents death in sepsis-induced mice.

BRIEF SUMMARY OF THE INVENTION

It is the object of this invention to use an extract of the Melothria Indica Lou plant, designated "Kas," as a therapeutic agent for the treatment of TNF-related diseases, such as sepsis.

It is another object of this invention to employ a method to isolate and to purify the active component Kas, which is present in the extract of the Melothria Indica Lou plant and inhibits the secretion of TNF by endotoxin-stimulated macrophages.

BRIEF DESCRIPTION OF THE DRAWINGS

FIG. 1: SCD Reverse-Phase Chromatography (PBS Elution) of The Extract of Melothria Indica Lou.

FIG. 2: Elisa Assay Of TNF-Alpha Released from LPS Macrophage in the Presence or Absence of the Aqueous Extract Of Melothria Indica Lou.

FIG. 3: SCD Reverse-Phase Chromatography (Organic Solvent Elution).

FIG. 4: RPP-100 Reverse-Phase Chromatography (Organic Solvent Elution).

FIG. 5: AX-100 Anion Exchange Chromatography (PBS Elution).

FIG. 6: AX-100 Anion Exchange Chromatography (PBS Gradient Elution).

FIG. 7: Silica Gel Chromatography.

DETAILED DESCRIPTION OF THE INVENTION

While the invention will be described in connection with preferred embodiments, it will be understood that it is not intended to limit the invention to those embodiments. On the contrary, it is intended to cover all alternatives, modifications, and equivalents as may be included within the spirit and scope of the invention as defined by the appended claims.

This patent application describes an extract from the Melothria Indica Lou plant for the inhibition of cytokines for the therapeutic treatment of disease such as sepsis.

1. Extract of the Melothria Indica Lou Inhibits TNF Secretion

Melothria Indica Lou is a popular herb emerging in certain asian countries such as India, Taiwan and Japan. It is a perennial plant that thrives on lowland, hillside and bushes of the above mentioned countries. The stems and/or leaves of Melothria Indica Lou are used as a herb that is believed to be beneficial to certain diseases such as cancer, soreness of the throat and acute conjunctivitis. We have discovered that the aqueous extract of Melothria Indica Lou contains an activity that blocks the release of TNF-alpha by endotoxin-stimulated macrophage. This finding is described as following:

a. Preparation of the Extract of Melothria Indica Lou

The fruit of Melothria Indica Lou was dried and chopped into small pieces. Thirty (30) grams of the dry material was extracted with 40 ml of hot (90–100° C.) phosphate buffer saline (PBS) for 10 minutes. The aqueous extract was collected by filtration.

b. Fractionation of the Aqueous Extract of Melothria Indica Lou

The aqueous extract (1 ml) was fractionated by a reverse phase HPLC column (SynChropak SCD, MICRA Scientific Inc., Northbrook, Ill.) by eluting the column isocratically with a chromatographic medium such as PBS. The elution profile is shown in FIG. 1. Fraction No. 6 was found to contain an activity blocking the release of TNF-alpha from LPS-stimulated macrophage by a TNF-alpha ELISA assay.

c. ELISA Assay for TNF-alpha

An ELISA assay kit purchased from R & D System (Minneapolis, Minn.) was used to assay TNF-alpha released from LPS-stimulated macrophage in the presence or absence of the aqueous extract of Melothria Indica Lou. The principle of ELISA assay is based on the capture of TNF by a TNF antibody followed by a secondary antibody that has been conjugated with an enzyme capable of the generation of a color reaction. The amount of TNF released by macrophage was quantified by the colormetric absorption at a certain wavelength.

As shown in FIG. 2, the left two wells marked with blank contain the TNF-alpha released by non-stimulated macrophage. The next two wells marked with L contain the TNF-alpha released by LPS-stimulated macrophage. The wells marked with 8, 10 and 12 contain the TNF-alpha released by LPS-stimulated macrophage in the presence of 8, 10 and 12 µl of Fraction No. 6 (see elution profile of SCD column) of the extract respectively. The intensity of the color, which reflects the amount of ENF released by the macrophages, clearly demonstrate that the Fraction No. 6 of the plant extract contains an activity blocking the release of TNF by macrophage.

2. Purification of Kas

Using the ELISA assay as described above, the active component inhibiting the release of TNF-alpha by LPS-stimulated macrophage was purified by the following procedure:

a. SCD Reverse Phase Chromatography (PBS Elution)

The aqueous extract (1 ml) was fractionated by a reverse phase HPLC column (SynChropak SCD, MICRA Scientific Inc. Northbrook, Ill.) by eluting the column isocratically with PBS. The elution profile was shown in FIG. 1. Fraction No. 6 was found to contain an activity blocking the release of TNF-alpha from LPS-stimulated macrophage by testing with a TNF-alpha ELISA assay.

b. SCD Reverse Phase Chromatography (Organic Solvent Elution)

Fraction No. 6 from the previous step was collected and applied to the same SCD reverse phase chromatography column equilibrated with H20:CH3CN=(50:50) containing 0.1% Trifluoroacetic acid. The column was isocratically eluted with the same solvent. The elution profile was shown in FIG. 3. Fraction Nos. 6 and 7 are found to contain an activity inhibiting the release of TNF-alpha by LPS-stimulated macrophage by testing with a TNF-alpha ELISA assay.

c. RPP Reverse Phase Chromatography

Fractions Nos. 6 and 7 collected from the previous step were applied onto a RPP reverse phase chromatography column (MICRA Scientific Inc. Northbrook, Ill.) equilibrated with 0.1% Trifluoroacetic acid in water. The column was eluted by a solvent gradient created by 0.1% Trifluoroacetic acid (solvent A) and H20:CH3CN=(50:50) containing 0.1% Trifluoroacetic acid (solvent B). The gradient was generated by 100% solvent A and 0% solvent B at time zero (0) followed by increasing solvent B from 0% to 100% after 20 ml elution volume. The elution profile was shown in FIG. 4. Fraction 2 was found to contain an activity inhibiting the release of TNF-alpha by LPS-stimulated macrophage by testing with a TNF-alpha ELISA assay.

d. AX-100 Anionic Exchange Chromatography (PBS Elution)

Fraction No. 2 collected from the previous step was applied onto a AX-100 anionic exchange chromatography column (MICRA Scientific Inc. Northbrook, Ill.) equilibrated with PBS. The column was eluted isocratically by PBS. The elution profile was shown in FIG. 5. Fractions Nos. 9 and 10 were found to contain an activity inhibiting the release of TNF-alpha by LPS-stimulated macrophage by testing with a TNF-alpha ELISA assay.

e. AX-100 Anion Exchange Chromatography (1/10 PBS—PBS Elution)

Fractions Nos. 9 and 10 collected from the previous step was applied onto a AX-100 anion exchange chromatography column (MICRA Scientific Inc. Northbrook, Ill.) equilibrated with 1:10 $H_2O$ dilution of PBS. The column was eluted by a solvent gradient created by 10% PBS in water (solvent A) and 100% PBS (solvent B). The gradient was generated by 100% solvent A and 0% solvent B at time zero followed by increasing solvent B from 0% to 100% after 20 ml elution volume. The elution profile was shown in FIG. 6. Fraction 2 was found to contain an activity inhibiting the release of TNF-alpha by ILPS-stimulated macrophage by testing with a TNF-alpha ELISA assay.

f. Silica Gel Chromatography

Fraction 2 from the previous step was applied onto a silica gel chromatography column (Partisil 5, Whatman) equilibrated with CH3CN:EtOH:H2O=84.5:15:0.5). The column was isocratically eluted with the same solvent. The elution profile was shown in FIG. 7. Fraction Nos. 6 and 7 are found to contain activity inhibiting the release of TNF-alpha by LPS-stimulated macrophage. This highly purified component was designated as Kas and was used for an animal study (mice sepsis) and a chemical structure study.

3. Kas Reduced Mortality Rate in Sepsis-induced Mice

The highly purified active component Kas, which inhibits TNF-alpha secretion and was extracted from the plant Melothria Indica Lou, was tested on a mice sepsis model. Balb/C mice (male) were intraperitoneally injected with galactosamine (15 mg/Kg body weight) and lipopolysaccharide (0.1, 1 and 10 µg/Kg body weight) with or without Kas (0.5, 25, 50 mg/Kg body weight). All mice were treated with a volume of 0.2 ml single injection with reagents mixed in pyrogen free saline. The mice were observed for seven (7) days.

The results are tabulated in Table I and indicate that Kas reduces the mortality of endotoxin-treated mice in a dose-dependent manner. In this model of sepsis using galactosamine and lipopolysaccharide, the $LD_{50}$ was established at 15 mg galactosamine per kilogram of body weight and 0.1 µg Lipopolysaccharide per kilogram of body weight. Using 1 mg or 0.5 mg of Kas reversed the mortality to give a 100% survival rate. Kas given at 0.01 mg/kg gave a 60% survival rate.

TABLE I

Effect of Kas on mortality in lethal toxicity produced in Balb/C mice using galactosamine and lipopolysaccharide.

| Galactosamine mg/kg | Lipopolysaccharide µg/kg | Kas mg/mouse | Mortality Dead/total | Percent Survival |
|---|---|---|---|---|
| 15 | 10 | — | 10/10 | 0 |
| 15 | 1 | — | 10/10 | 0 |
| 15 | 0.1 | — | 6/10 | 40 |
| 15 | — | — | 0/10 | 100 |
| — | 0.1 | — | 0/10 | 100 |
| 15 | 0.1 | 1 | 0/10 | 100 |
| 15 | 0.1 | 0.5 | 0/10 | 100 |
| 15 | 0.1 | 0.01 | 4/10 | 60 |

I claim:

1. A method of treatment of sepsis by administering Kas extracted from *Melothria indica* Lou to subjects having sepsis in sufficient dosages for sufficient duration to effectively treat said sepsis.

2. The method of treatment of sepsis of claim 1 wherein the dosage of Kas is between about 0.01 mg/kg and about 1 mg/kg.

3. The method of treatment of sepsis of claim 1 wherein the dosage of Kas is between about 0.01 mg/kg and about 0.5 mg/kg.

4. The method of treatment of sepsis of claim 1 wherein the dosage of Kas is between about 0.5 mg/kg and about 1 mg/kg.

* * * * *